(12) United States Patent
Travis (10) Patent No.: US 6,541,510 B2
(45) Date of Patent: Apr. 1, 2003

(54) ANTIVIRAL METHODS AND COMPOUNDS

(75) Inventor: Craig R. Travis, South Miami, FL (US)

(73) Assignee: Immugen Pharmaceuticals, Inc., South Miami, FL (US)

( * ) Notice: Subject to any disclaimer, the term of this patent is extended or adjusted under 35 U.S.C. 154(b) by 0 days.

(21) Appl. No.: 09/967,341

(22) Filed: Sep. 28, 2001

(65) Prior Publication Data

US 2002/0068738 A1 Jun. 6, 2002

Related U.S. Application Data (60) Provisional application No. 60/236,425, filed on Sep. 28, 2000.

(51) Int. Cl.[7] .............................................. A61K 31/353
(52) U.S. Cl. ........................................................ 514/456
(58) Field of Search ......................................... 514/456

(56) References Cited

U.S. PATENT DOCUMENTS 4,315,862 A   2/1982   Elsohly et al.

OTHER PUBLICATIONS

Nahas et al., *Chemical Abstracs*, 87 (1), 1977.
Formukong et al., *J. Pharm. Pharmacol.*, 41, 705–709 (1989).
Nathan et al., *Can. . Physiol. Pharmacol.*, 70, 1305–1308 (1992).
Burstein et al., *J. Pharmacol. and Experimental Therapeutics*, 251, No. 2, 531–535 (1989).
Akamanchi et al., *Pharm. Pharmacol. Commun.*, 5, 323–329 (1999).
Kitagawa et al., *Chem. Pharm. Bull.*, 39 (4), 1062–1064 (1991).
Jobin et al., *Thromb. Diath. Haemorrh.*, 22 (3), 466–481 (1969).

*Primary Examiner*—Joseph K. McKane
*Assistant Examiner*—Rebecca Anderson
(74) *Attorney, Agent, or Firm*—Leydig, Voit & Mayer Ltd.

(57) ABSTRACT

The invention provides a method, compounds, and compositions for inhibiting the replication or proliferation of a virus. In accordance with the invention, at least one cannabichromene derivative is exposed to the virus, a host cell, or an infected cell under conditions sufficient to inhibit the replication or proliferation of the virus.

14 Claims, 2 Drawing Sheets

ANTIVIRAL METHODS AND COMPOUNDS

BACKGROUND OF THE INVENTION

Unfettered viral infection and proliferation afflicts most aspects of human life. For example, health and vitality are indirectly impacted by unchecked microbial growth. In this respect, viruses cause food and water spoilage and associated sickness. Viruses also reduce food yield and safety and hinder agriculture and aquaculture. Of course, viruses represent a direct health threat as well, insofar as they are causative agents of many human and animal diseases. Many approaches to controlling viral growth and proliferation have been described. Indeed, one of the hallmarks of the last century of medicine is the development of antibiotic and antiviral agents. However, many such agents are rapidly losing their effectiveness as viruses evolve resistance to such agents. Well-known examples of this acquired resistance include influenza and immunodeficiency viruses (e.g., HIV, SIV, FIV, etc.). Furthermore, many antiviral agents have undesired side effects and pose attendant health concerns over extended periods of time. In light of the state of the art, there continues to exist a need for methods and compounds to control viral replication and proliferation, particularly to control or treat viral diseases.

BRIEF SUMMARY OF THE INVENTION

The invention provides a method, compounds, and compositions for inhibiting the replication or proliferation of a virus. In accordance with the invention, at least one cannabichromene derivative is used to treat (e.g., exposed to) the virus, a host cell, or an infected cell under conditions sufficient to inhibit the replication or proliferation of the virus. These and other advantages of the invention, as well as additional inventive features, will be apparent upon reading the following description of the invention and from the drawings.

DETAILED DESCRIPTION OF THE INVENTION

Within the context of the present method, the virus can be any, such as, for example, herpesviruses (e.g., HSV 1 and 2), papillomaviruses (e.g., HPV serotypes), influenza viruses, immunodeficiency viruses (e.g., serotypes of HIV, SIV, FIV, and the like), etc. A particularly preferred virus to combat by way of the present inventive method is HIV.

In accordance with the inventive method, at least one cannabichromene derivative is exposed to the virus, a host cell, or an infected cell. In this context, a host cell is any cell or type of cell, which the desired virus can infect, which are generally known in the art vis-á-vis their respective viruses. In this respect, for example, it is generally known that HIV can infect cells such as CD40+ lymphocytes; HIV cells can transiently infect epithelial cells and lie dormant in neurological tissues, etc. Further in the context of the present invention, an infected cell is one harboring at least one component of the targeted virus (e.g., its genome or a portion thereof). Typically, infected cells can reproduce the virus and thereby mature virions are replicated under permissive conditions (which may include the introduction of additional components into the cell).

The invention further provides novel cannabichromene derivative(s), which can be used in the inventive method and which have the following formula:

wherein, $R^1$, $R^3$, $R^5$, and $R^6$ can optionally be —$COR^1$, —$COR^3$, —$COR^5$, and/or —$COR^6$, respectively, and preferably $R^3$ is —$COR^3$, and wherein R can otherwise be as follows:

$R^1$ is:
a) H,
b) a $C_{1-4}$ alkyl group or ester thereof,
c) COOH,
d) OH,
e) a O—$C_{1-5}$ alkyl (preferably $OCH_3$) or alkanoyl, optionally substituted by mono- or di-methylamino or ethylamino groups,
f) a O—CO—$C_{3-10}$ alkyl group containing a carboxyl or amino group,
g)

wherein n=1 to 8
h) a p-aminobenzyl group or a $C_{1-7}$ aminoalkyl group or an organic or mineral acid addition salt thereof, an isocyanate or isothiocyanate derivative of the p-aminobenzyl or aminoalkyl group, a carboxyl terminated derivative of the aminoalkyl group having from 1 to 7 additional carbon atoms or a salt thereof, and an activated derivative of the carboxyl terminated derivative;
i) $R^1$ and $R^2$ comprise a substituent of the formula —$O(CH_2)_{3-5}$, wherein $R^1$ and $R^2$, together with the carbon atoms to which they are bonded, comprises a ring where at least one hydrogen atom thereof is optionally substituted with a halogen (e.g., fluorine, bromine, iodine, astatine);
j) a lactone (e.g., COCOH); or
k) $CH(CH_3)CO_2H$ or —$OCOCH_3$ $R^2$ is:
a) H, OH, COOH, or a halogen
b) $C_{1-6}$ carboxy or alkoxy group, or
c) $R^1$ and $R^2$ comprise a substituent of the formula —$O(CH_2)_{3-5}$, wherein $R^1$ and $R^2$, together with the carbon atoms to which they are bonded, comprises a ring where at least one hydrogen atom thereof is optionally substituted with a halogen.

$R^3$ is:
a) $(W)_m$—Y—$(Z)_m$, wherein
W is a $C_{5-12}$ straight or branched (preferably $1S'CH_3$, $2R'CH_3$ dimethyl) alkyl (e.g., -pentyl, -hexyl, -heptyl, -octyl, or -nonyl), alkenyl, alkynyl, group, or mixture thereof, optionally substituted with at least one halogen (e.g., halogen terminal group or even dihalogen), Y is a bond, O, S, SO, $SO_2$, CO, NH, N($C_{1-6}$ alkyl), or NCS, Z is:
  i) a $C_{5-12}$ alkyl, alkenyl, alkynyl, group, or mixture thereof, optionally substituted with at least one halogen, optionally substituted with a terminal aromatic ring,
  ii) $CN_{1-3}$, $CO_2H$, or $CO_2C_{1-4}$ alkyl, $CONH_2$, $CONHC_{1-4}$ alkyl, or $CON(C_{1-4}$ alkyl$)_2$, wherein each $C_{1-4}$ alkyl on the amide nitrogen can be the same or different, or
  iii) a phenyl or benzyl group, optionally substituted with halo, $C_{1-6}$ alkyl, $C_{1-6}$ alkoxy, $C_{1-6}$ alkylthio, CN, $CF_3$, $CO_2H$, or $CO_2C_{1-4}$ alkyl, $CONH_2$, $CONHC_{1-4}$ alkyl, or $CON(C_{1-4}$ alkyl$)_2$, wherein each $C_{1-4}$ alkyl on the amide nitrogen can be the same or different, and wherein m and n are the same or different, and each is either 0 or 1, b) a $C_{5-12}$ alkyl or haloalkyl group, optionally substituted with a terminal aromatic ring, $CN_{1-3}$, NCS, $CO_2H$, or $CO_2C_{1-4}$ alkyl, $CONH_2$, $CONHC_{1-4}$ alkyl, or $CON(C_{1-4}$ alkyl$)_2$, wherein each $C_{1-4}$ alkyl on the amide nitrogen can be the same or different, or c) a $C_{5-12}$ alkene or alkyne group, optionally substituted with a halogen, dithiolene, terminal aromatic ring, $CN_{1-3}$, NCS, $CO_2H$, or $CO_2C_{1-4}$ alkyl, $CONH_2$, $CONHC_{1-4}$ alkyl, or $CON(C_{1-4}$ alkyl$)_2$, wherein each $C_{1-4}$ alkyl on the amide nitrogen can be the same or different;

$R^6$ is selected from the group consisting of:
  a) hydrogen,
  b) hydroxy or lactone,
  c) halo,
  d) $C_{1-6}$ alkoxy, $C_{1-6}$ alkylthio, $C_{1-6}$ alkyl, or $C_{1-6}$ haloalkyl,
  e) CN,
  f) $N_3$,
  g) $CO_2H$,
  h) $CO_2$-$C_{1-4}$ alkyl,
  i) C(Y)(Z)—OH,
  j) C(Y)(Z)—O—$C_{1-4}$ alkyl, and
  k) $C_{1-6}$ alkyl-$CO_2$—Y,
wherein Y and Z are each independently H or $C_{1-6}$ alkyl, $R^7$ is selected from the group consisting of:
  a) hydrogen,
  b) hydroxy or lactone,
  c) halo,
  d) $C_{1-6}$ alkoxy, $C_{1-6}$ alkylthio, $C_{1-6}$ alkyl, or $C_{1-6}$ haloalkyl,
  e) CN,
  f) $N_3$,
  g) $CO_2H$,
  h) $CO_2$—$C_{1-4}$ alkyl,
  i) C(Y)(Z)—OH,
  j) C(Y)(Z)—O—$C_{1-4}$ alkyl,
  k) $C_{1-6}$ alkyl-$CO_2$—Y, and
  l) =O or =S;
wherein Y and Z are each independently H or $C_{1-6}$ alkyl, $R^{12}$ and $R^{12'}$ together form =O or =S, or each is independently selected from the group consisting of:
  a) hydrogen,
  b) hydroxy or lactone,
  c) halo,
  b) $C_{1-6}$ alkoxy, $C_{1-6}$ alkylthio, $C_{1-6}$ alkyl, or $C_{1-6}$ haloalkyl,
  c) CN,
  d) $N_3$,
  d) $CO_2H$,
  e) $CO_2$—$C_{1-4}$ alkyl,
  f) C(Y)(Z)—OH,
  g) C(Y)(Z)—O—$C_{1-4}$ alkyl, and
  h) $C_{1-6}$ alkyl-$CO_2$—Y,
wherein Y and Z are each independently H or $C_{1-6}$ alkyl,

Q is:
  a) O or S, or
  b) N—W, wherein W is:
    i) hydrogen,
    ii) $C_{1-6}$ alkoxyalkyl, $C_{1-6}$ alkyl, or $C_{1-6}$ haloalkyl
    iii) $OC_{1-6}$ alkyl, or $OC_{1-6}$ haloalkyl,
    iv) CN,
    v) $C_{1-6}$ alkyl,
    vi) C(Y)(Z)$C_{1-4}$ alkyl, or
    vii) $C_{1-6}$ alkyl-$CO_2$—Z,
wherein Y and Z are each independently H or $C_{1-6}$ alkyl.

The cannabichromene derivative preferably includes a lactone, H, OH or $OCH_3$, methyl, —CH($CH_3$)$CO_2H$, or —$OCOCH_3$ as $R^1$ substituents. Preferred substituents at $R^2$ are hydrogen, halogen (most preferably fluorine) hydroxyl, COOH, or methoxyl groups. Preferably, $R^6$ is H, OH, lactone, halogen, $C_{1-6}$ alkoxy, or $C_{1-6}$ alkyl, most preferably methyl. $R^7$ preferably is H, OH, halogen, or COOH and most preferably hydrogen. $R^{12}$ and $R^{12'}$ are each independently H, OH, lactone, halogen, $C_{1-6}$ alkoxy, or $C_{1-6}$ alkyl and most preferably methyl. Desirably, the bond between C7 and C8 is a double bond, but, as indicated, it can be a single bond. Also, Q preferably is oxygen.

Preferred substituents at $R^3$ include:
  a) $(W)_m$—Y—$(Z)_m$, wherein
    W is a $C_{5-12}$ alkyl, alkenyl, alkynyl (e.g., 2'-ynyl, 3'-ynyl or 4'-ynyl), group, or mixture thereof, optionally substituted with at least one halogen,
    Y is a bond, O, S, SO, SO2, CO, NH, N($C_{1-6}$ alkyl), or NCS,
    Z is:
      i) a $C_{5-12}$ alkyl, alkenyl, alkynyl (e.g., 2'-ynyl, 3'-ynyl or 4'-ynyl), group, or mixture thereof, optionally substituted with at least one halogen, optionally substituted with a terminal aromatic ring,
      ii) $CN_{1-3}$, $CO_2H$, or $CO_2C_{1-4}$ alkyl, $CONH_2$, $CONHC_{1-4}$ alkyl, or $CON(C_{1-4}$ alkyl$)_2$, wherein each $C_{1-4}$ alkyl on the amide nitrogen can be the same or different, or
      iii) a phenyl or benzyl group, optionally substituted with halo, C1-6 alkyl, $C_{1-6}$ alkoxy, $C_{1-6}$ alkylthio, CN, $CF_3$, $CO_2H$, or $CO_2C_{1-4}$ alkyl, $CONH_2$, $CONHC_{1-4}$ alkyl, or $CON(C_{1-4}$ alkyl$)_2$, wherein each $C_{1-4}$ alkyl on the amide nitrogen can be the same or different,
    wherein at least one of W and Z includes a branched chain and wherein m and n are the same or different, and each is either 0 or 1,
  b) a terminally-branched (e.g., terminal dimethyl) $C_{5-12}$ alkyl or haloalkyl group, optionally substituted with a terminal aromatic ring, $CN_{1-3}$, NCS, $CO_2H$, or $CO_2C_{1-4}$ alkyl, $CONH_2$, $CONHC_{1-4}$ alkyl, or CON ($C_{1-4}$ alkyl$)_2$, wherein each $C_{1-4}$ alkyl on the amide nitrogen can be the same or different, or c) a terminally-branched $C_{5-12}$ alkene or alkyne group, optionally substituted with a halogen, dithiolene, terminal aromatic ring, $CN_{1-3}$, NCS, $CO_2H$, or $CO_2C_{1-4}$ alkyl, $CONH_2$, $CONHC_{1-4}$ alkyl, or $CON(C_{1-4}$ alkyl$)_2$, wherein each $C_{1-4}$ alkyl on the amide nitrogen can be the same or different.

Particularly preferred $R^3$ substituents include $C_5$–$C_{12}$ alkynes, and particularly preferred groups also include di- or tri-methyl terminal groups. A most preferred substituent at $R^3$ is a dimethylheptyl, particularly 1'S, 2'R, and also preferably with terminal halogen (or dihalogen) substituents, and another preferred substituent is 5,5-diimethyl hex(1-ene)(3-yne)yl. Other preferred $R^3$ substituents include:

wherein $W_1$ is H, methyl, or ethyl, wherein $W_2$ and $W_3$ are each independently H or methyl, wherein at least one of $W_1$, $W_2$, and $W_3$ is other than H and/or halogenated, and wherein $W_4$ is a $C_{1-4}$ alkyl or haloalkyl, optionally substituted with an aromatic ring. Preferably, $R^3$ is a branched $C_{6-12}$ alkyl group containing at least one double bond (more preferably at position $C_4$–$C_{10}$), and preferably the chain has an odd number of carbon atoms. More preferably, $R^3$ is terminally branched or contains a terminal double bond, and the invention provides compounds according to Formulas I–V having such substituents. More preferably, $R^3$ preferably is dimethylheptyl (DMH) (e.g., 1',1' DMH or 1'R, 2'S DMH), dimethylhexyl, or dimethylpentyl. For example, $R^3$ can be a di- tri- or tetramethylpentyl, -hexyl, or -heptyl, etc., chain (e.g., 1,1,5-trimethylhexyl, 1,1,5,5-tetramethylhexyl, or 1,1, 5-trimethyl-hept-4-enyl). In some instances, the $R^3$ substituent can have bulky terminal moieties, for example, methyl, dimethyl, $(CH_2)_{1-6}$—$CON(CH_3)_2$, or $C_{6-12}$ haloalkyl with halogenated terminal carbon atoms (preferably bromine).

In the context of this invention, halogenated alkanes, alkenes, and alkynes can have any number of halogen substitutions. In a preferred embodiment, the halogenated alkane, alkene, or alkyne has at least one halogen on a terminal carbon atom (e.g., $CX_{1-3}$, wherein X is halogen). Alkyl groups (as well as alkenes and alkynes) can be straight chain or branched. Moreover, the compounds can exist as a single stereoisomer or a mixture of stereoisomers (e.g., a racemic mixture), or a single geometric isomer,(e.g., E, Z, cis or trans) or a mixture of geometric isomers, all of which are within the scope of the invention.

Many cannabichromene derivatives are known, and others can be synthesized using methods that are known in the art (see, e.g., U.S. Pat. Nos. 4,315,862 and 4,837,228). Other exemplary compounds include:

Formula g

Formula h

Formula i

Formula j

In carrying out the inventive method, the desired compound is exposed to the virus, a host cell, or an infected cell under conditions sufficient to inhibit the growth or replication of the virus in question (or a population of like viruses). For use in vitro, between about 0.1 µg/ml and about 50 µg/ml (such as, for example, between about 1.0 µg/ml and about 25 µg/ml or even between about 5 µg/ml and about 15 µg/ml) would be an appropriate concentration. The method can be employed to control viral growth under a variety of conditions. For example, the method can be employed ex vivo to control viral growth or replication. In this respect, the invention can be used in agricultural applications to curtail viral growth on crops or on produce. The method can be employed in aquaculture to reduce the effect of viral infection of fish or other raised species. The method can be employed to control the growth of undesired viruses domestically (e.g., in household applications) such as, for example, in food, water, and other common household products.

Depending on the desired use, the compound can be formulated into an appropriate composition. In this respect, the invention pertains to the use of a cannabichromene derivative as described herein to prepare an antiviral composition. In one embodiment, the compositions can be an agriculturally-acceptable composition. Such composition can be formulated, for example, to deliver the compound to plants, fields, lawns, orchards, lakes or other agricultural targets. Examples of suitable agricultural compositions are known in the art and include, for example, wettable powders, dry flowables, microencapsulation of effective agents, liquid or solid formulations and antibiotic fractions obtained from suitable cultures (see, e.g., U.S. Pat. Nos. 5,061,495 and 5,049,379). Such compositions can be formulated in powder, granular, pellet or bait form with solid carriers. Alternatively, such compositions can be formulated as liquids for dusting or spraying.

In other applications, the cannabichromene compound(s) can be employed therapeutically or prophylactically to ward off or treat viral infections in vivo. For such use, the compound is desirably formulated into a pharmacologically-acceptable (i.e., pharmaceutically- or physiologically-acceptable) composition including a suitable carrier, and optionally other inactive or active ingredients. Such compositions are suitable for delivery by a variety of commonly-employed routes of delivery, such as, for example, buccal, sublingual, dermal, intraocular, intraotical, pulmonary, transdermal, intralymphatic, intratumor, intracavitary, intranasal, subcutaneous, implantable, inhalable, intradermal, rectal, vaginal, transmucosal, intramuscular, intravenous and intraarticular routes, among many others. Depending on the desired manner of application, the composition can include adjuvants, bile salts, biodegradable polymers and co-polymers, buffers, chelating agents, colorants, diluents, emollients, emulsifiers, enzyme inhibitors, hydrogels, hydrophilic agents, lipoproteins and other fatty acid derivatives, liposomes and other micelles, microporous membranes, mucoadhesives, neutral and hydrophobic polymers and copolymers, particulate systems, perfumes, salt forming acids and bases, semi-permeable membranes, single or multiple enteric coatings, solvents (e.g., alcohols, dimethyl sulfoxide (DMSO), etc.), surfactants, viral envelope proteins, or other ingredients.

In one of its forms, a pharmacologically-acceptable composition can be an inhalable formulation comprising an aerosol of liquid or solid particles, such as are known in the art. Application of the composition via inhalation can treat bronchial conditions associated with inflammation (e.g., the common cold (rhinovirus), influenza, etc.). This formulation can further comprise additional agents such as preservatives, antioxidants, flavoring agents, volatile oils, buffering agents, dispersants, surfactants, and the like, as are known in the art. Such formulation can also be provided with an inhalant, or in the inhalant, either in unit form or in a form that permits its repetitive use.

A pharmacologically-acceptable composition can also be a topical formulation (e.g., ointment, cream, lotion, paste, gel, spray, aerosol oil, etc.), wherein the carrier is a diluent for the agent suitable for topical delivery, e.g., petrolatum, lanoline, polyethylene glycols, alcohols and the like, optionally including trans-dermal enhancers. In the topical formulation, the carrier may be in a form suitable for formulating creams, gels, ointments, sprays, aerosols, patches, solutions, suspensions and emulsions.

A pharmacologically-acceptable composition can also be formulated for oral delivery, for example in the form of capsules, cachets, lozenges, tablets, powder, granules, solutions, suspensions, emulsions, essential oils (particularly hemp seed oil), etc. Such formulations typically include aqueous or non-aqueous liquid solutions and suspensions (e.g., oil-in-water or water-in-oil emulsions). Such oral formulations typically are encased in an enteric coating.

Examples of oral formulations are buccal or sub-lingual formulations comprising lozenges which can also comprise flavoring agents and other known ingredients, or pastilles which can also comprise an inert base containing, for example, gelatin, glycerin, sucrose, acacia, and other ingredients and fillers as is known to the practitioner.

A pharmacologically-acceptable composition can also be a parenteral formulation, such as injectable solutions and suspensions. Typically, such formulations also comprise agents such as antioxidants, buffers, anti-bacterial agents, other anti-viral agents such as direct acting inhibitors of replication, and solutes which render the solution or suspension isotonic with the blood of an intended recipient. The solutions or suspensions are typically sterile aqueous or non-aqueous injectable solutions or suspensions, and can also comprise suspending agents and thickening agents. This formulation is generally provided in a sealed ampule or vial.

A pharmacologically-acceptable composition can also be a slow release formulation, which, when administered or applied to a subject, is capable of releasing a desired amount of the compound(s) over a pre-determined period of time. Alternatively, the composition can be a transdermal formulation, in which the carrier is suitable for facilitating the transdermal delivery of the agent. Examples are aqueous and alcoholic solutions, DMSO, oily solutions and suspensions, and oil-in-water or water-in-oil emulsions. A transdermal formulation can also be an iontophoretic transdermal formulation, in which typically the carrier can be an aqueous and/or alcoholic solution, an oily solution or suspension and an oil-in-water and water-in-oil emulsion. This formulation can further comprise a transdermal transport promoting agent, and be provided in the form of a kit with a transdermal delivery device, preferably an iontophoretic delivery device, many variations of which are known in the art.

Additional formulations of a pharmacologically-acceptable composition include, but are not limited to an implantable capsule or cartridge (e.g., for tissue implantation), a patch, an implant, or a suppository (e.g., for rectal or transmucosal administration). Typically, the composition will be distributed, either to physicians or to patients, in an administration kit, and the invention provides such a kit. Typically, such kits include, in separate containers, an administration device (e.g., syringes and needles, inhalators, pills, suppositories, transdermal delivery devices, etc) and a plurality of unit dosages of the composition as described above. In some kits, the composition can be preformulated. Other kits include separate ingredients for formulating the composition. The kit can additionally comprise a carrier or diluent, a case, and instructions for formulating the composition (if applicable) and for employing the appropriate administration device.

In carrying out the inventive method in vivo, the composition can be delivered to a patient in any amount and over any time course suitable for producing the desired therapeutic effect, and one of skill in the art will be able to determine an acceptable dosing schedule. Typically, the composition is delivered to a patient between 1 and about 6 times a day, if not continuously through transdermal or time release formulations. However, in some applications, it is appropriate to administer the composition less often. Generally each dose is between about 2 mg/m$^3$ to about 1000 mg/m$^3$, and more preferably about 0.01 mg/kg/day, about 1 mg/kg/day, such as about 10 ng/kg/day to about 10 mg/kg/day, and can be up to about 100 mg/kg/day (e.g., about 250 mg/kg/day). These dosages can be somewhat reduced when the composition is employed in combination with other agents, and especially when the cytochrome $P_{450}$ system is attenuated (e.g., through the adjunctive administration of cannibidiol derivatives). Of course, as some patients can develop tolerance to one or more compounds within the composition over the course of treatment, the dosage amount and/or schedule can be adjusted as appropriate. Moreover, the dosage amount and schedule can be reduced as a patient responds favorably to treatment and/or if any toxic side effects are noted.

In addition to employing a compound such as the cannabichromene derivative(s) as set forth herein, a pharmacologically-acceptable composition including the cannabichromene derivative can be adjunctively employed as well. For example, the method can include the adjunctive administration of antineoplastics, antitumor agents, antibiotics, antifungals, other antivirals (particularly antiretroviral compounds), antihelminthic, and antiparasitic compounds. Exemplary antiviral agents suitable for adjunctive use in the inventive method include abacavir, azidothymidine cidofovir, delavirdine mesylate, didanosine, dideoxycytidine, efavirenz, foscarnet, ganciclovir, indinavir sulfate, lamivudine, nelfinavir mesylate, nevirapine, ritonavir, saquinavir, saquinavir mesylate, stavudine, zalcitabine, etc. In treating tumors or neoplastic growths, suitable adjunctive compounds can include anthracycline antibiotics (such as doxorubicin, daunorubicin, carinomycin, N-acetyladriamycin, rubidazone, 5-imidodaunomycin, and N-acetyldaunomycin, and epirubicin) and plant alkaloids (such as vincristine, vinblastine, etoposide, ellipticine and camptothecin), paclitaxel and docetaxol, mitotane, cisplatin, phenesterine, etc. Anti-inflammatory therapeutic agents suitable for adjunctive use in the present invention include steroids and non-steroidal anti-inflammatory compounds, (such as prednisone, methyl-prednisolone, paramethazone, 1,1-fludrocortisol or fluorocortisone, triamciniolone, betamethasone and dexamethasone, ibuprofen, piroxicam, beclomethasone; methotrexate, azaribine, etretinate, anthralin, psoralins); salicylates (such as aspirin; and immunosuppressant agents such as cyclosporine). Additional pharmacologic agents suitable for adjunctive use in the inventive method include anesthetics (such as methoxyflurane, isoflurane, enflurane, halothane, and benzocaine); antiulceratives (such as cimetidine); antiseizure medications (such as barbituates; azothioprine (an immunosuppressant and antirheumatic agent); and muscle relaxants (such as dantrolene and diazepam). Moreover, the method can be employed in conjunction with specific antibody therapies or steroid therapies in treating autoimmune diseases. Other pharmacologically-active agents that can be adjunctively employed in conjunction with the composition include 5'-alkyl resorcinol derivatives or other constituents of natural marijuana having antimicrobial or anti-inflammatory activities (e.g., cannabinol and/or its derivatives, cannibidiol and/or its derivatives, cannabigerol and/or its derivatives, cannabinolic acid and its derivatives, cannabidiolic acid and its derivatives, terpenoids, flavanoids (e.g., cannflavin), etc. (see, e.g., U.S. Pat. No. 6,274,635).

The composition can include biologically active agents, such as lymphokines or cytokines, anti-inflammatory, anti-bacterial, anti-viral, anti-fungal, anti-parasitic, anti-metabolic, anti-inflammatory, vasoactive, anti-neoplastic, bronchoacting, local anesthetic, immunomodulating, enzymatic, hormonal, growth promoting and regenerating agents, as well as neurotransmitters, and cell receptor proteins and ligands, among many other agents. Examples of other biological agents are analgesics (such as acetominophen, anilerdine, aspirin, buprenorphine, butabital, butorphanol, choline salicylate, codeine, dezocine, diclofenac, diflunisal, dihydrocodeine, elcatonin, etodolac, fenoprofen, hydrocodone, hydromorphone, ibuprofen, ketoprofen, ketorolac, levorphanol, magnesium salicylate, meclofenamate, mefenamic acid, meperidine, methadone, methotrimeprazine, morphine, nalbuphine, naproxen, opium, oxycodone, oxymorphone, pentazocine, phenobarbital, propoxyphene, salsalate, sodium salicylate, tramadol and narcotic analgesics in addition to those listed above). Anti-anxiety agents are also useful including alprazolam, bromazepam, buspirone, chlordiazepoxide, chlormezanone, clorazepate, diazepam, halazepam, hydroxyzine, ketaszolam, lorazepam, meprobamate, oxazepam and prazepam, among others. Other biologically-active agents include anti-anxiety agents associated with mental depression, such as chlordiazepoxide, amitriptyline, loxapine, maprotiline, and perphenazine, among others. Examples of other active ingredients include anti-inflammatory agents such as non-rheumatic aspirin, choline salicylate, diclofenac, diflunisal, etodolac, fenoprofen, floctafenine, flurbiprofen, ibuprofen, indomethacin, ketoprofen, lidomide, magnesium salicylate, meclofenamate, mefenamic acid, nabumetone, naproxen, oxaprozin, phenylbutazone, piroxicam, salsalate, sodium salicylate, sulindac, tenoxicam, tiaprofenic acid, thalidomide, linomide, and tolmetin, as well as anti-inflammatories for ocular treatment (such as diclofenac, flurbiprofen, indomethacin, ketorolac, and rimexolone (generally for post-operative treatment)), and anti-inflammatories for non-infectious nasal applications (such as beclomethaxone, budesonide, dexamethasone, flunisolide, triamcinolone, and the like); soporifics (anti-insomnia/sleep inducing agents) such as those utilized for treatment of insomnia, including alprazolam, bromazepam, diazepam, diphenhydramine, doxylamine, estazolam, flurazepam, halazepam, ketazolam, lorazepam, nitrazepam, prazepam quazepam, temazepam, triazolam, zolpidem and sopiclonei among others; sedatives including diphenhydramine, hydroxyzine, methotrimeprazine, promethazine, propofol, melatonin, trimeprazine, and the like; sedatives and agents used for treatment of petit mal seizures and tremors, among other conditions, such as amitriptyline HCl; chlordiazepoxide, amobarbital; secobarbital, aprobarbital, butabarbital, ethchlorvynol, glutethimide, L-tryptophan, mephobarbital, methohexital sodium salt, midazolam HCl, oxazepam, pentobarbital Na, Phenobarbital, secobarbital sodium salt, thiamylal sodium, and many others. Other active compounds can include agents used in the treatment of head trauma (brain injury/ischemia), such as enadoline HCl (e.g., for treatment of severe head injury), cytoprotective agents, and agents for the treatment of menopause, menopausal symptoms (treatment), e.g., ergotamine, belladonna alkaloids and phenobarbital, for the treatment of menopausal vasomotor symptoms, e.g., clonidine, conjugated estrogens and medroxyprogesterone, estradiol, estradiol cypionate, estradiol valerate, estrogens, conjugated estrogens, esterified estrone, estropipate, and ethinyl estradiol. Examples of agents for treatment of pre menstrual syndrome (PMS) are progesterone, progestin, gonadotrophic releasing hormone, oral contraceptives, danazol, luprolide acetate, vitamin B6; agents for treatment of emotional/psychiatric treatments such as tricyclic antidepressants including amitriptyline HCl (Elavil), amitriptyline HCl, perphenazine (Triavil) and doxepin HCl (Sinequan). Examples of tranquilizers, anti-depressants and anti-anxiety agents are diazepam (Valium), lorazepam (Ativan), alpra-zolam (Xanax), SSRI's (selective Seratonin reuptake inhibitors), fluoxetine HCl (Prozac), sertaline HCl (Zoloft), paroxetine HCl (Paxil), fluvoxamine maleate (Luvox) venlafaxine HCl (Effexor), serotonin, serotonin agonists (Fenfluramine); antibiotics (e.g., fluoroquinolones and tetracycline); antihistamines; catabolic steroids; and vasoactive agents (e.g., beta-blockers and pentoxiphylline (Trental)). Other compounds include cannabinoids such as CT-3 and HU-210.

EXAMPLES

While one of skill in the art is fully able to practice the instant invention upon reading the foregoing detailed description, the following examples will help elucidate some of its features. Of course, as these examples are presented for purely illustrative purposes, they should not be used to construe the scope of the invention in a limited manner, but rather should be seen as expanding upon the foregoing description of the invention as a whole.

Example 1

This example demonstrates the synthesis of an alkylated resorcinol.

A mixture of 2,6-dimethoxyphenol (73.4 g, 0.48 mole), 2,6-dimethyl-2-heptanol (69.0 g, 0.48 mole) and methanesulfonic acid (95 mL) was stirred at 50° C. for 3 h and then at room temperature overnight. The mixture was poured over ice-water (600 mL) with stirring. The mixture was extracted with $CH_2Cl_2$ (2×200 mL). The extracts were washed with water, saturated aqueous $NaHCO_3$, saturated aqueous sodium chloride solution and dried over anhydrous $Na_2SO_4$. The solution was concentrated under reduced pressure to obtain the product as an oil (130 g, 96%). Analysis of this substance (MS (FAB) m/z 281 (MH)$^+$; $^1$H NMR ($CDCl_3$) δ0.80 (d, 6H), 1.0–1.1 (m, 4H), 1.27 (s, 6H), 1.40–1.60 (m, 3H), 3.89 (s, 6H), 5.36 (s, 1H), 6.54 (s, 2H)) revealed it to be 4-(1,1,5-trimethylhexyl)-2,6-dimethoxyphenol:

Example 2

This example demonstrates the synthesis of an alkylated resorcinol.

To solution of crude 4-(1,1,5-trimethylhexyl)-2,6-dimethoxyphenol from Example 1 (0.19 g, 0.68 mmol) in dry THF (6 mL) was added iodomethane (0.78 g, 5.4 mmol). The mixture was treated with 60% dispersion of sodium hydride in mineral oil (0.06 g, 1.5 mmol) under nitrogen atmosphere. The mixture was stirred at room temperature for 24 h and then concentrated under reduced pressure. The residue was treated with ether (20 mL). Water (5 mL) was added cautiously. The layers were separated, the ether layer was washed with water (5 mL), dried ($MgSO_4$) and concentrated under reduced pressure. The crude product was purified by chromatography over a column of sillica using cyclohexane/EtOAc 6:1 as the eluent to obtain 0.17 g (85%) of the product. Analysis of this substance (MS (FAB) m/z

295 (MH)+. 1H NMR (CDCl$_3$) δ0.81 (d, 6H), 1.0–1.2 (m, 4H), 1.28 (s, 6H), 1.40–1.60 (m, 3H), 3.84 (s, 3H), 3.87 (s, 6H), 6.53 (s, 2H)) revealed it to be 1-(1,1,5-Trimethylhexyl)-3,4,5-trimethoxybenzene (referred to hereinafter as IG-07):

Example 3

This example demonstrates the synthesis of a cannabichromene derivative.

A solution of 1-(1,1,5-Trimethylhexyl)-3,4,5-trimethoxybenzene from Example 2 (0.344 g, 1.5 mmol) and geraniol (0.348 g, 1.5 mmol) and p-toluenesulfonic acid (0.03 g) in dry benzene (50 mL) was heated at reflux for 2 h. The mixture was concentrated to dryness. The crude product was purified by chromatography over preparative thick layer plates (2×0.25 mm) using cyclohexane:EtOAc 5:1 as the developing solvent followed by chromatography over a column of silica using cylcohexane/EtOAc 95:5 as the eluent to obtain 0.107 g (20%) of the product. Analysis of the compound (MS (FAB) m/z 373 (MH)+. 1H NMR (CDCl3) δ 0.80 (d, 6H), 1.0–1.2 (m, 4H), 1.21 (s, 6H), 1.31 (s, 3H), 1.4–1.51 (m, 2H), 1.52–1.7 (m, 9H), 1.7–1.9 (m, 2H), 2.0–2.15 (m, 2H), 2.60 (t, 2H), 4.56 (s, 1H), 5.1 (m, 1H), 6.31 (s, 1H), 6.39 (s, 1H)) revealed it to be 3,4-Dihydro-2-methyl-2-(4-methyl-3-pentenyl)-7-( 1,1,5-trimethylhexyl)-2H-1-benzopyran-5-ol (referred to hereinafter as IG-08):

Example 4

This example demonstrates that the cannabichromene compounds exhibit antiretroviral activity.

Test Material

Solutions of IG-07 and IG-08 in 100% DMSO were prepared. Cannabidiol was purchased from Sigma Chemical (St Louis, Mo.), and solubilizedi in 100% DMSO. All stocks in DMSO were stored frozen at −20 ° C., and thawed immediately before use. Light precautions were used during stock preparation and assay set-up to minimize the exposure of the solubilized compounds to ambient light during handling.

PBMC Isolation and Blasting:

Peripheral blood monocular cells (PBMCs) were obtained from normal hepatitis and HIV-1 negative donors by ficoll hypaque gradient separation. The mononuclear cells were washed to remove residual separation media, counted, viability determined and resuspended in RPMI 1640 medium supplemented with 15 % FBS (heat inactivated), 2 mM L-glutamine, 100 U/mL penicillin, 100 µg/mL streptomycin, and 10 µg/mL gentamycin with 2 µg/mL phytohemagluttin (PHA) at 1×10$^6$ cells/mL. The cells were cultured for 48 to 72 h at 37 ° C., 5% CO$_2$. Following incubation, cells were collected by centrifugation, washed and resuspended in RPMI 1640 supplemented with 15% FBS (heat inactivated), 2 mM L-glutamine, 100 U/mL penicillin, 100 µg/mL streptomycin, and 10 µg/mL gentamycin with 20 U/mL recombinant IL-2 (R & D Systems, Minneapolis, Minn.). IL-2 was included in the culture medium to maintain the cell division initiated by the PHA mitogenic stimulation, and promote optimal growing conditions for the PBMCs. The cultures were then maintained until use by ½ culture volume change with fresh IL-2 containing medium every 3 days.

PBMC Assay:

Human peripheral blood mononuclear cells from a minimum of 2 donors, that have been blasted with PHA and IL-2, were counted, viability determined by Trypan Blue dye exclusion and mixed in equal ratios. Pooled donors were used to minimize the variability observed between individual donors which results from quantitative and qualitative differences in HIV infection and overall response to the PHA and IL-2 of primary lymphocyte populations. The cells were resuspended at 1×10$^6$ cells/mL in RPMI 1640 without phenol red supplemented with 15% Fetal Bovine Serum (heat inactivated), 2 mM L-glutamine, 100 U/mL penicillin, 100 µg/mL streptomycin, 10 µg/mL gentamycin and IL-2 (20 U/mL, R&D Systems, Minneapolis, Minn.). Fifty microliters of cells were then distributed to the inner 60 wells of a 96 well round bottom microtiter culture plate in a standard format developed by the Infectious Disease Research department of Southern Research Institute. Each plate contains cell control wells (cells only), virus control wells (cells plus virus), and experimental wells (drug plus cells plus virus). Alternatively, cells were cultured in T25 cm$^2$ or T75 cm$^2$ tissue culture flasks at a starting density of 1×10$^6$ cells per ml. Serially diluted compounds were added to the microtiter plate or tissue culture flask followed by the appropriate pre-titered strain of HIV-1. For virus replication inhibition experiments the HIV-1 strain RoJo was used. This is a low passage presumable subtype B pediatric isolate with a syncytium inducing (SI) phenotype in MT-2 cells isolated by Southern Research Institute personnel. All samples were assayed in triplicate where possible with an accompanying determination of compound toxicity. The final volume per well in the microtiter plates was 200 µL. The final volume in the tissue culture flask varied depending upon experimental design and flask size. Assays were incubated for 6 days in a humidified atmosphere at 37° C., 5% CO$_2$, after which supernatants were collected, for analysis of RT activity and cell viability by MTS dye reduction. Culture were also examined microscopically, any abnormalities noted, and in the case of tissue culture flasks cell counts and viability determined by Trypan Blue Dye exclusion.

PBMC Time-of-Addition Assays/Attachment Assays

Time-of-addition assays were performed with PBMCs in two ways. For both assays, PBMCs were isolated and cultured under the conditions as described above. Time-of-addition assays were carried out in either a tissue culture flask format (T-75 cm$^2$) or in microtiter wells. In both cases due to the lack of plastic adherence and heterogeneity of the PBMC population for susceptibility to infection, it was not possible to use complete removal of virus following a timed adsorption to synchronize the infection and limit the assay to a single round of infection. Therefore, serial washing by partial removal of the media was used to reduce the concentration of virus and compound (if required) in the assay. Compound addition in relationship to antiviral activity was either assessed over a short addition interval immediately before or after virus addition or for up to 72 h post infection. For all assays virus replication was assessed at 6 days of culture by determining RT expression in cell-free supernatants. In the tissue culture flask format cells were counted and Trypan Blue Dye exclusion used to monitor compound cytotoxicity. Cell viability in the 96 well microtiter plate format was determined by MTS dye reduction. AZT was used as a positive control.

cAMP Determinations

Cyclic AMP determinations were performed on PBMC lysates using an enzyme immunoassay (EIA) kit obtained from Cayman Chemical (Kit#581001, Ann Arbor, Mich.). PBMCs following treatment with compounds were lysed and processed as described in the kit for quantitation of cAMP expression. Processing of samples, construction of standard curves and quantitation of the cAMP content of unknowns were carried out per manufacturers instructions. Following determination of the amount of cAMP per sample, activity was re-expressed as pMol cAMP per $1 \times 10^6$ viable cells, using microscopic cell counts with Trypan Blue Dye exclusion. Initial experiments carried out with the Adenylate Cyclase Activation FlashPlate® Assay (NEN Life Science Products Boston, Mass.) are not presented due to poor reproducibility and detection using this system.

Flow Cytometry

Flow cytometry studies were carried out on PHA/IL-2 induced PBMCs treated for 6 days with the various test compounds. Prior to flow cytometry the PBMCs were washed, counted and $1 \times 10^6$ cells resuspended in PBS and stained for CD4 or CD8 surface markers using anti-CD4.PE or CD8.PE (both from PharMingen) for 30 min at 4° C. The PBMC were then washed, fixed (Cytofix) and permeabilized (Cytoperm) followed by staining for apoptosis-related DNA damage. Initial experiments used the BrdU Flow Kit from PharMigen (2354KK). This kit with the appropriate software should have yielded percent apoptosis along with the number of cells in each phase of the cell cycle. However, we were not successful with this kit and subsequently used the data to look at only the distribution in the cell cycle of the PBMCs following drug treatment. We were successful in detecting apoptosis in PBMCs with the PharMingen APO-BRDU™ kit (6576KK). Using this kit, we were not able to co-stain for CD4 and CD8 due to the fluorescent tags used in the APO-BRDU™ kit. For both kits, manufacturers instructions were followed for staining and analysis of the samples. Following the appropriate staining protocol the cells were analyzed using a Becton Dickinson (Bedford, Mass.) FACSSort MTS Staining for Cell Viability:

At assay termination the assay plates were stained with the soluble tetrazolium-based dye MTS (CellTiter96® Reagent Promega) to determine cell viability and quantify compound toxicity. MTS is metabolized by the mitochondria enzymes of metabolically active cells to a soluble formazan product, allowing the rapid quantitative analysis cell viability and compound cytotoxicity. This reagent is a single stable solution that does not require preparation before use. At termination of the assay 20 µL of MTS reagent was added per well and incubated for 4 h at 37° C. Adhesive plate sealers were used in place of the lids, the sealed plate was inverted several times to mix the soluble formazan product and the plate was read spectrophotometrically at 490 nm with a Molecular Devices Vmax plate reader.

Reverse Transcriptase Assay for Culture Supernatants:

Reverse transcriptase activity was measured in cell-free supernatants. Tritiated thymidine triphosphate (NEN) (TTP) was resuspended in distilled $H_2O$ at 5 Ci/mL. Poly rA and oligo dT were prepared as a stock solution which was kept at −20° C. The RT reaction buffer was prepared fresh on a daily basis and consists of 125 µL 1.0 M EGTA, 125 µL $dH_2O$, 110 µL 10% SDS, 50 µL 1.0 M Tris (pH 7.4),50 µL 1.0 M DTT, and 40 µL 1.0 M $MgCl_2$. These three solutions were mixed together in a ratio of 2 parts TTP, 1 part poly rA:oligo dT, and 1 part reaction buffer. Ten microliters of this reaction mixture was placed in a round bottom microtiter plate and 15 µL of virus containing supernatant was added and mixed. The plate was incubated at 37° C. in a water bath with a solid support to prevent submersion of the plate and incubated for 60 minutes. Following reaction, the reaction volume was spotted onto pieces of DE81 paper, washed 5 times for 5 minutes each in a 5% sodium phosphate buffer, 2 times for 1 minute each in distilled water, 2 times for 1 minute each in 70% ethanol, and then dried. Opti-Fluor O was added to each sample and incorporated radioactivity was quantitated utilizing a Wallac 1450 Microbetaplus liquid scintillation counter.

P24 Antigen ELISA:

ELISA kits were purchased from Coulter Electronics. The assay was performed according to the manufacturer's instructions. Control curves were generated in each assay to accurately quantitate the amount of p24 antigen in each sample. For experiments using cell lysates. Fifty thousand ($5 \times 10^4$) viable cells were lysed in Coulter ELISA buffer and subjected to 1 round of freeze/thawed to liberate trapped p24 and p24 detected per manufacturers instructions. HIV capsid protein (p24) was quantitated spectrophotometrically at 450 nm using a Molecular Devices Vmax plate reader using a standard curve. Final concentrations were calculated from the optical density values using the Molecular Devices Soft Max software package.

Attachment Assay:

The attachment assay was performed with the HeLa CD4 LTR β-gal cells available from the AIDS Research and Reference Reagent Repository. HeLa cells do not express cell surface CD4, express the HIV coreceptor CXCR4 and are not infectable by HIV-1 unless CD4 is present. HeLa CD4 LTR β-gal cells express cell surface CD4 and contain an LTR β-galactosidase reporter construct. Upon infection either the Tat protein incorporated into the virion or new Tat produced following virus integration and transcription transactivates the LTR β-gal reporter, leading to expression of the β-galactosidase enzyme. HeLa CD4 LTR β-gal cells are routinely cultured with the required selection antibiotics and screened for mycoplasma contamination. Twenty-four h prior to initiation of the assay cells were trypsinized, counted and $1 \times 10^4$ cells placed in a 0.2 cm well in media without selection antibiotics. Media was removed at 24 h and compound in media placed on the cells and incubated for 15 to 30 min at 37° C. A known titer of virus was then added to the wells and the incubation continued for 1 h. At the end of the incubation the wells were washed 6 times with media and the culture continued for 48 h. At 48 h the wells were washed one time with PBS and β-galactosidase enzyme expression determined by chemiluminescence per manufacturers instructions (Tropix Gal-screen™, Tropix, Bedford, Mass.). Compound toxicity was monitored on sister plates using MTS dye reduction.

The attachment assay with PBMCs was performed as follows. Briefly, $1 \times 10^6$ PHA/IL-2 PBMCs were incubated for 0, 2, 4 and 24 hours with IMG compounds and cannabidiol in polypropylene tubes. A pre-titered amount of HIV-1 (96USHIPS7 strain, obtained from the AIDS Research and Reference Reagent Program) was added in the presence of compound and incubated for 3 h at 37° C. After incubation the cultures were washed 3 times (400×g, 10 min, 4° C.) with media (1:25,000 dilution of input p24), the cell pellets lysed with p24 lysing buffer (Coulter) and p24 content determined by ELISA.

Fusion Assay.

This assay uses the HeLa CD4 LTR β-gal and HL2–3 cells available from the AIDS Research and Reference Reagent Repository. The HL2/3 are derived from HeLa cells and engineered to express HIV gp120 on their cell surface and Tat protein in their cytoplasma. Thus following gp120/CD4/coreceptor-mediated fusion; cytoplasmic mixing results in the HL2/3 cell-derived Tat trans-activation of the β-galactosidase reporter. Both cell lines were maintained as suggested by the AIDS Research and Reference Reagent Repository. Twenty-four h prior to initiation of the assay cells were trypsinized, counted and $5 \times 10^3$ cells placed in a 0.2 cm well in media without selection antibiotics. To initiate the fusion assay HeLa CD4 LTR β-gal ($5 \times 10^3$ cells per 0.2 cm well) were incubated with compound for 1 h at 37° C. HL2/3 cells ($5 \times 10^3$) were added to the 0.2 cm well and the incubation continued for 48 h. At 48 h the wells were washed 1 time with PBS and β-galactosidase enzyme expression determined by chemiluminescence per manufacturers instructions (Tropix Gal-screen™, Tropix, Bedford, Mass.). Compound toxicity was monitored on sister plates using MTS dye reduction.

Data Analysis:

Using a computer program, $IC_{50}$ (50%, inhibition of virus replication), $I_{50}$ (inhibitory concentration 50%) $TC_{50}$ (50% reduction in cell viability) and a therapeutic index (TI, $IC_{50}/TC_{50}$) were calculated for all antiviral assessments.

Results

Inhibition of Virus Attachment and Fusion

The effect of the test compounds was assessed using assays designed to monitor inhibition of HIV attachment and fusion. Two experiments using HeLa CD4 LTR β-gal cells are summarized in Table 1. In these experiments, either the attachment assays with virus added 15 min after compound addition or following pre-treatment of the cells for 4 or 24 h with the compounds was performed. The data demonstrate that the IG-07 and IG-08 compounds as well as cannabidiol had a variable effect on HeLa CD4 LTR β-gal cell viability. In the first experiment the compounds did not alter cell viability, while in the second cyotoxicity appeared to correlate with exposure time. Because this is a 48 h assay, variability with cytotoxic compound is often observed and is dependent upon the density and health of the cells at the initiation of the assay. Therefore all the compounds are potentially altering the viability of the HeLa CD4 LTR β-gal cells. In addition to the effect on cell viability several compounds suppressed β-galactosidase production below background (cells alone+compounds: IG-07, IG-08, and cannabidiol at all times). In addition, transient suppression of virus replication at lower concentrations of compounds was observed consistently with IG-07. These observations were consistent throughout two independent experiments and were not found in the positive control assays using Chicago Sky Blue (CSB). Additionally, the assays performed with CSB met all internal assays validation criteria for an acceptable assay. Therefore, these data suggest that the IG-07 and G-08 interact with HeLa CD4 LTR β-gal cells altering their ability to induce β-galactosidase either through a specific (alteration in transcription or protein production) or non-specific (cytotoxic) pathway.

TABLE 1

Effect of the IMG Compounds and Cannabidiol in the HeLa CD4 LTR β-gal HIV-1 Attachment Assay.

| Cmpd. | Pretreat (h) | Experiment 1 | | Experiment 2 | | Comment |
|---|---|---|---|---|---|---|
| | | $IC_{50}$ | $TC_{50}$ | $IC_{50}$ | $TC_{50}$ | |
| CSB (μg/ml) | 0 | 1.1 | >10 | 0.17 | >10 | Positive control |
| | 4 | 1.71 | >10 | 2.11 | >10 | |
| | 24 | 1.3 | >10 | 4.7 | >10 | |
| IG-07 (μM) | 0 | >50 | >50 | 16 | >50 | Transient suppression lost with at lower concentrations |
| | 4 | >50 | >50 | >50 | >50 | Transient suppression lost with at lower concentrations |
| | 24 | >50 | >50 | >50 | >50 | Transient suppression t lost with at lower concentrations |
| IG-08 (μM) | 0 | 16 | >50 | 0.9 | >50 | Suppression of μ-galactosidase activity, Transient suppression lost with at lower concentrations |
| | 4 | 10.8 | >50 | 11 | 29 | Suppression of μ-galactosidase activity |
| | 24 | 7.4 | >50 | 2.6 | 12.2 | Suppression of μ-galactosidase activity, Transient suppression lost with at lower concentration |

In addition to assessing inhibition of attachment with HeLa CD4 LTR β-gal cells a standard virus fusion assay was performed using HeLa CD4 LTR β-gal and HL2/3 cells assay we did not employ timed addition of the test compounds, but rather was performed to verify that the effects of the compounds on the HeLa CD4 LTR β-gal cells β-galactosidase expression. Table 2 summarizes these data, which demonstrate that although the compound effects in the fusion assay on the HeLa CD4 LTR β-gal cells are not as pronounced as the attachment assay the effects are still present.

TABLE 2

Effect of the IMG Compounds and Cannabidiol in the HeLa CD4 LTR β-gal/HL2/3 HIV-1 Fusion Assay.

| Compound | Antiviral Activity | | Comments |
|---|---|---|---|
| | $IC_{50}$ | $TC_{50}$ | |
| CSB (μg/ml) | 1.75 | >10 | Positive control |
| IG-07 | >50 | >50 | |
| IG-08 | 29.9 | 36.5 | |
| Cannabidiol | 19.3 | 39.8 | Suppression of β-galactosidase activity |

Two observations suggest antiviral activity via targets other than specific or non-specific inhibition of virus attachment/entry. The consistent inhibition of HIV attachment/entry seen in HeLa CD4 LTR β-gal cells following a 24 h pre-incubation with IG-08 and cannabidiol, but not IM507, suggests that the interaction of the compounds with the cells are different. The overall reduction in β-galactosidase activity in untreated cells also suggests either a specific anti-HIV LTR or non-specific cellular suppression of transcription/translation by the compounds.

Time-of-Addition Studies

Time-of-addition studies with PBMCs were initially proposed based upon the clients hypothesis that the IMG compounds and cannabidiol were modulating antiviral activity through specific coreceptor interactions and second messenger pathways. Therefore initial studies were designed to look at the effect of pretreatment on antiviral activity. The first time-of-addition assay are summarized in Table 4.

TABLE 4

Time-of-addition Assay with PBMC (Addition Prior to Infection)

| Compounds (μM) | Pre-Treat (h) | $IC_{50}$ | TI | Comments |
|---|---|---|---|---|
| AZT | 0 | 0.0013 | >3077 | No significant change in TI or $IC_{50}$ |
| | 2 | 0.0011 | >3636 | |
| | 4 | 0.0011 | >3636 | |
| | 24 | 0.0031 | >1290 | |
| IG-07 | 0 | 6.9 | 17 | No significant change in TI or $IC_{50}$ |
| | 2 | 6.1 | 19.9 | |
| | 4 | 5.3 | 22.7 | |
| | 24 | 10.8 | 11.1 | |
| IG-08 | 0 | 14.2 | 3.5 | 4-fold decrease in $IC_{50}$ 4 h pretreatment |
| | 2 | 10.4 | 4.8 | |
| | 4 | 4.1 | 12 | |
| | 24 | 11.9 | 4.2 | |
| Cannabidiol | 0 | 0.58 | 83 | Initial 10-fold loss of activity at 2, regain 3.3-fold at 4 h then a 17-fold increase 4.6 in $IC_{50}$ at 24 h pretreatment overall |
| | 2 | 5 | 9.7 | |
| | 4 | 1.5 | 33 | |
| | 24 | 10.5 | 4.6 | |

This experiment identified some significant effects of pretreatment of PBMCs with the compounds and cannabidiol. Compound IG-07 showed no significant change in $IC_{50}$ with pretreatment for up to 24 h (approximately 2-fold increase at 24 h). These changes are within an expected 3-fold error for the assay for $IC_{50}$ as seem in the range of the $IC_{50}$ for AZT from 1.1 to 3.1 nM. Thus the antiviral target for IG-07 is independent of early effects on the PBMCs and does not involve modulation of coreceptors. IG-08 showed transient decreases in $IC_{50}$ at 4 hours. A decrease in $IC_{50}$ translates to an increase in antiviral potency since the compound exerted a constant amount of cellular cyotoxicity ($IC_{50}$). The other pre-treatment times did not show a significant change from addition of the compounds with the virus. This pattern of activity suggests that pretreatment with IG-08 modulates a cellular pathway directly responsible for the potency of the antiviral response, such as a signaling pathways regulating transcriptional factor expression or compound metabolism. Since enhanced IG-08 did not correlate with attachment inhibition, the data suggest a mechanism of action independent of a virus entry pathway. The pattern observed for cannabidiol is more complex. It looses approximately 10-fold of its potency with a 2 h pretreatment, partially regains potency (3.3 fold decrease in $IC_{50}$) at 4 h pretreatment and then looses any gains at 24 h (total loss in potency 17-fold).

In a second time-of-addition assay, pre-treatment was coupled with post-treatment. Compounds added at −4, 0 and +6 h in relationship to addition of virus showed the expected modulations in $IC_{50}$ with pretreatment, but also showed no difference between adding the compound at infection or 6 h post infection in antiviral potency (Table 5). In these experiments AZT exhibited the expected enhancement of activity (4.6-fold) with a 4 h preincubation, demonstrating that it requires phosphorylation before it is active. Therefore the results at +6 h with cannabidiol and the IG compounds suggests that although they can modulate the antiviral outcome in pre-treatment scenarios, such modulations are not the primary mechanism of antiviral action.

TABLE 5

Time-of-addition Assay (Addition at −4, 0 and +6 H Relative to Infection)

| Compound | Treatment | Antiviral activity (μM) | | |
|---|---|---|---|---|
| | | $IC_{50}$ | $TC_{50}$ | TI |
| AZT | −4 h pre | 0.0008 | >4 | >5000 |
| | At infection | 0.0037 | >4 | >1081 |
| | 6 h Post | 0.0046 | >4 | >869 |
| IG-07 | −4 h pre | 39.5 | >100 | >2.5 |
| | At infection | 67 | >100 | >1.5 |
| | 6 h post | 46.1 | >100 | >2.2 |
| IG-08 | −4 h pre | 6.2 | >100 | >16 |
| | At infection | 15.7 | >100 | >6.3 |
| | 6 h post | 22.5 | >100 | >4.4 |
| Cannabidiol | −4 h pre | 12.1 | >100 | >8.3 |
| | At infection | 13.8 | >100 | >7.3 |
| | 6 h post | 12.1 | >100 | >8.3 |

The activity of the IG compounds and cannabidiol was further assessed in a time-of-addition assay aimed at investigating the effects of the compounds on events in virus replication from virus entry to completion of reverse transcription using peripheral blood mononuclear cells (PBMC). Initial infection in PBMCs is difficult to synchronize, due to non-adherence to tissue culture substrates and the heterogeneity of PBMC populations, resulting in a frequency of initial frequency of infection of CD4[+] lymphocytes of less than 10%. These characteristics prevent the simple and reproducible detection of HIV replication early in the infection. Thus PBMC-based time-of-addition assays were allowed to go through multiple rounds of infection to allow sufficient virus replication to assess the effects of inhibitors. In this regard, reverse transcription is complete between 32 and 48 h post infection. Thus, for purposes of the assay, sufficient reverse transcription has occurred that the total virus expression at 6 days (RT) allows a statistically relevant comparison with the treatment groups. While additional rounds of infection are still occurring during this time the previous rounds of infection have already established sufficient virus expression that further rounds of infection do not contribute to overall virus expression. For this assay, the compounds were added during the interval from virus entry to completion of reverse transcription. The relative $IC_{50}$ for each treatment at 6 days was calculated; this value shows the relative potency of the compounds when added after virus exposure (See FIG. 1). The results for each time point at the lowest concentration which results in complete suppression of virus replication when compound is added simultaneously with the virus also was plotted as a Maximal Suppression Graph (see FIG. 2).

Figure 1:
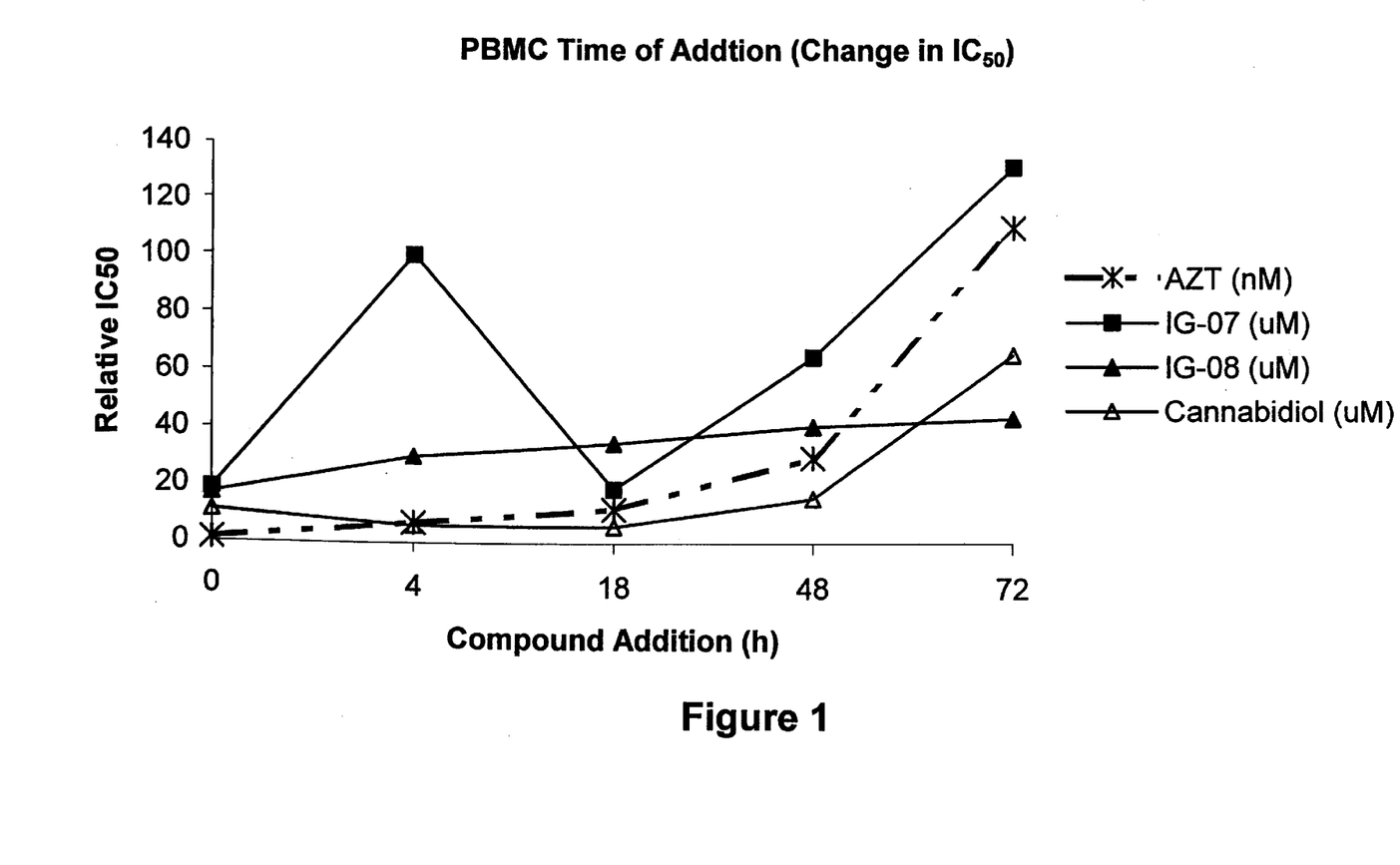
FIG. 1 graphically illustrates the results of a PBMC time-of-addition assay in terms of relative IC50s values.
Figure 2:
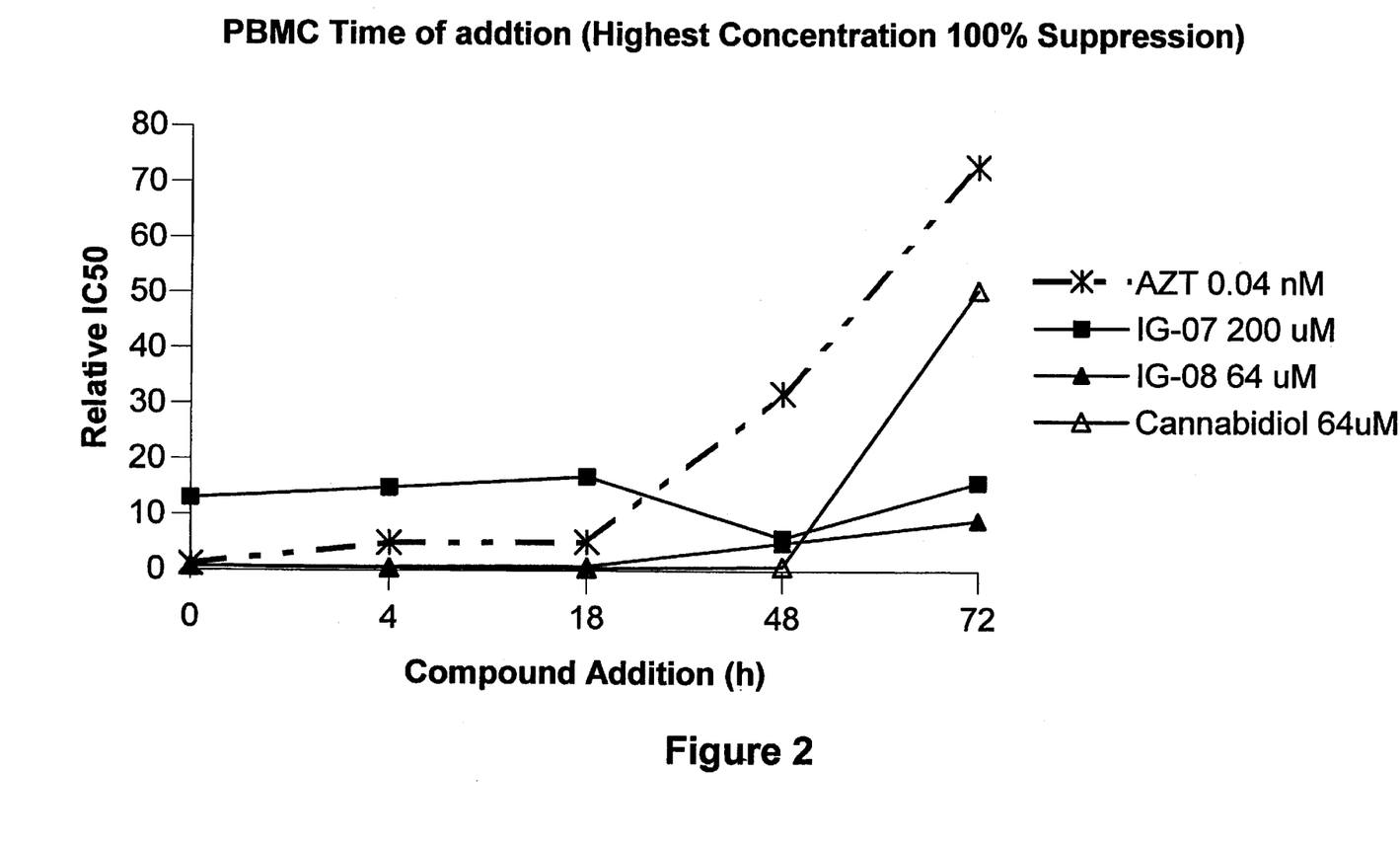
FIG. 2 graphically illustrates the results of a PBMC time-of-addition assay in terms antiviral activity versus maximal suppression of virus replication at time 0.

Comparison of the data presented in FIGS. 1 and 2 suggests that all compounds have an antiviral target present after completion of reverse transcription. From these data, IG-08 appears to interact with an antiviral target other than virus entry or reverse transcription, whereas IG-07 appears to interact with antiviral targets prior to and coinciding with reverse transcription. Cannabidiol displays a pattern of inhibition similar to the post 48 h suppression of virus replication that the IG congeners display. However, the data suggest that the IG compounds are potentially more potent in their interaction with the antiviral target.

Thus in toto the time-of-addition studies suggest that the cannabichromene compound (IG-08) interacts with antiviral targets and is potentially more potent in its interaction with its antiviral targets than cannabidiol. Moreover, although IG-08 appears to be able to modulate the antiviral response when pre-exposed to the cells, its primary mechanism of action appears to involve an antiviral target post entry and completion of reverse transcription.

Flow Cytometry Studies

Experiments were conducted using flow cytometry to assess the effect of the IMG compounds and cannabidiol on induction of apoptosis. Briefly, compound-treated PBMCs were assayed for apoptosis using a BrdU methodology. Table 6 summarizes the effects of the IMG Compounds on cell cycle and cell viability by Trypan Blue Dye exclusion. These effects are further summarized in Table 7. Table 7 reduces the changes in the cell cycle to a ratio based upon the percent of cells in $G_2$-$G_1$, $G_2$-$G_1$ cells represent transition cells that are in either $G_2$ or $G_1$, that cannot be distinguished based upon DNA content by flow cytometry. As seen in these experiments, the number of cells remains relative constant in the PBMC population (Table 6) and can be used to generate a ratio to compare the cells in other phases of the cell cycle. This ratio cannot be used as a quantitative factor to measure fold-increases or decreases between population, but rather to access tends in the cell cycle.

TABLE 6

Cell Cycle Analysis of PBMCs Treated with the IMG Compounds and Cannabidiol

| Cmpd. | µM | HIV | % Viable Cells | % 7-AAD positive per cell cycle phase | | | |
|---|---|---|---|---|---|---|---|
| | | | | $G_0$-$G_1$ | $G_2$-M | S | $G_2$-$G_1$ |
| Control | | − | 90 ± 9 | 92 ± 1.9 | 5.6 ± 1.8 | 1.9 ± 2.8 | 2 ± 0.6 |
| | | + | 79 ± 9 | 90.4 ± 2.1 | 5.7 ± 4.2 | 3.7 ± 5.6 | 2 ± 0 |
| IG-07 | 5 | − | 92 | 89 | 6.9 | 0 | 2 |
| | | + | 94 | 89 | 10 | 0 | 2 |
| | 100 | − | 50 | 94 | 0.2 | 6 | 2 |
| | | + | 55 | 95 | 3.1 | 1.7 | 2 |
| IG-08 | 15 | − | 89 | 91 | 8.7 | 0 | 2 |
| | | + | 94 | 98 | 0.08 | 2.4 | 2 |
| | 30 | − | 62 | 98 | 0.6 | 1 | 2 |
| | | + | 67 | 99 | 0.15 | 0.9 | 2 |
| Cannabidiol | 1 | − | 85 | 91 | 9.2 | 0 | 2 |
| | | + | 94 | 94 | 5.7 | 0 | 2 |
| | 25 | − | 86 | 96.4 | 0.05 | 3.6 | 2 |
| | | + | 55 | 96 | 0 | 4.2 | 2 |
| | 35 | − | 61 | 95.5 | 0 | 4.5 | 2 |
| | | + | 61 | 98 | 0 | 2.6 | 2 |

TABLE 7

Summary of the Effects of the Compounds on Cell Cycle in Infected and Uninfected PBMCs

| | | Proportion of Cells in: $G_0$-$G_1$:$G_2$-M:S:$G_2$-$G_1$ | |
|---|---|---|---|
| Cmpd. | Viability | uninfected cells | Infected Cells |
| Controls | | 45:3:1:1 | 45:1:1:1 |
| IG-07 | High | 45:5:0:1 | 45:5:0:1 |
| | Low | 47:0:3:1 | 48:2:1:1 |
| IG-08 | High | 46:4:0:1 | 49:0:1:1 |
| | Low | 49:0:0:1 | 50:0:0:1 |
| Cannabidiol | High | 46:5:0:1 | 47:3:0:1 |
| | Low | 48:0:2:1 | 49:0:1:1 |

The IG compounds had effects on the cell cycle in both uninfected and infected cells, and the effects were concentration dependent. In uninfected cells at non-cytotoxic concentrations the primary effect appeared to be reduction in the proportion of cells in S phase with minor changes in $G_0$-$G_1$ and $G_2$-M. Thus, these cells have reduced DNA synthesis, which will eventually have a downward effect on the number of cells in mitosis and therefore the number of cells capable of reproducing the virus. At concentrations near the $TC_{50}$ in uninfected cells, two patterns emerged. The first was an increase in S phase (IG-07 and cannabidiol). The second was a total reduction in S and $G_2$-M (IG-08) with an increase in cells in $G_0$-$G_1$. Of the two patterns displayed the one for IG-08 appears to identify a true cytostatic population of cells, while that observed for the other compounds appears to be a more intermediate position. In any event, these experiments evince that that all tested compounds promote cytostasis in a dose dependent fashion in uninfected cells.

In HIV-infected PBMCs at non-cytotoxic concentrations the primary effect appears to be a reduction in S phase with a concomitant increase in cells in $G_2$-M. This suggests that at lower concentrations in HIV-infected cells that entry into S phase is blocked or slowed significantly and raise the possibility of a second block at the $G_2$-M boundary. This occurs with all compounds except IG-08, which shows a decrease in $G_2$-M and an increase in $G_0$-$G_1$, without a significant effect on S. This observation suggests that S phase is possible, but that rather than progressing to $G_2$-M, the cells are returning to $G_0$-$G_1$ and/or being eliminated.

At higher concentrations near the $TC_{50}$ in infected cells two patterns also emerge. One pattern is seen in IG-07 and partially in cannabidiol, where higher concentrations of compound reversed the increase in $G_2$-M seen at lower concentrations and the cell cycle profile returns to normal. This suggests that the cells pilling up in S phase were eliminated and possibly accounts for the loss in total cell viability. The pattern seen with cannabidiol actually appears to be lagging slightly behind that of IG-07. The final pattern seen with IG-08 is a complete loss of cells in $G_2$-M and S phase with a build-up of cells in $G_0$-$G_1$. This is similar to that seen in uninfected cells at high concentrations and suggests a block before S phase and cytostasis. This is also consistent with prior suggestions that target cells in the $G_0$ or $G_1$ a phase of the cell cycle might be refractory for reverse transcription of HIV (see, e.g., Korin et al., *J Virol.*, 72(4), 3161–68 (1998)).

These data in toto show that the IG compounds and cannabidiol alter the progression of PBMCs through the cell cycle. These changes start at antiviral concentrations, but do not become significant until cytotoxic concentrations are reached.

In another series of experiments, the IG compounds and cannabidiol treated cells were assessed for the induction of apoptosis (see Tables 8 and 9). The positive control (kit and Fas ligand) indicated that this apoptosis procedure is working as predicted. As IL-2 is an essential component for maintaining the health of PHA induced PBMCs, a second focus of these studies focuses on the effect of the compounds in the absence of IL-2. Tables 8 and 9 show that inclusion of IL-2 slightly increased apoptosis in uninfected cells, but does not alter apoptosis in infected cells. Infection increased apoptosis in infected PBMCs supplemented with IL-2 by 4% and by 6.7 % in IL-2 deficient PBMCs. Thus IL-2 deficient cells are more fragile and likely to undergo apoptosis. In the presence of IL-2 apoptosis was seen only in cannabidiol at the high test concentrations at or above the compounds normal $TC_{50}$. In cannabidiol-treated PBMCs significant apoptosis (>2-fold change from control) was seen only in infected cells. When IL-2 was removed, increased apoptosis was observed seen in IG-0-treated cells, indicating that the compounds could induce apoptosis in the absence of IL-2. These results indicate that the IG compounds are not mediating the majority of their antiviral activity through induction of apoptosis. However they do show that the compounds can induce apoptosis at higher concentration and in non-IL2 stimulated cells. Therefore, the IG compounds can induce apoptosis, but the apoptosis observed is directly correlated with cytotoxic aspects of the compounds and not a primary mechanism of modulating infected cell survival.

TABLE 8

Summary of the Effect of the IMG Compounds and Cannabidiol on PBMC Apoptosis in IL-2 Supplemented Media

| Sample | Conc. µM | HIV | % Apoptosis | Fold Change |
|---|---|---|---|---|
| Kit – control | | | 0.52% | |
| Kit + control | | | 36% | |
| FAS | | – | 17.8 | |
| | | + | 17.3 | |
| PBMC + IL-2 | | – | 12 | 1 |
| | | + | 16.1 | 1 |
| AZT | 1 | – | 15.0 | 1.3 |
| | | + | 13.3 | 0.8 |
| IG-07 | 100 | – | 22.8 | 2 |
| | | + | 22.5 | 1.4 |
| | 50 | – | 14.4 | 1.2 |
| | | + | 16 | 1 |
| IG-08 | 30 | – | 27.5 | 2.3 |
| | | + | 32.1 | 2 |
| | 15 | – | 17.3 | 1.2 |
| | | + | 19.3 | 1.2 |
| Cannabidiol 30 µM | 30 | – | 22 | 1.8 |
| | | + | 74 | 4.6 |
| | 15 | – | 20.5 | 1.7 |
| | | + | 20.0 | 1.2 |

TABLE 9

Summary of the Effect of the IMG Compounds and Cannabidiol on PBMC Apoptosis in IL-2 Deficient Media

| Sample | Conc. µM | HIV | % Apoptosis |
|---|---|---|---|
| Kit – control | | | 0.52% |
| Kit + control | | | 36% |
| PBMC + FAS | | – | 13.7 |
| | | + | 16.2 |
| PBMC no IL-2 | | – | 9.5 |
| | | + | 16.2 |
| AZT | 1 | – | 15.1 |
| | | + | 13.7 |
| IG-07 | 100 | – | 54 |
| | | + | 64 |
| | 50 | – | 27 |
| | | + | 32.6 |
| IG-08 | 30 | – | 11.7 |
| | | + | 13.8 |
| | 15 | – | 18.4 |
| | | + | 29 |
| Cannabidiol | 30 | – | ND |
| | | + | ND |
| | 15 | – | ND |
| | | + | ND |

Wait — Table 9 has a "1" column too. Actually looking again, Table 9 shows fold change values as well:

| Sample | Conc. µM | HIV | % Apoptosis | |
|---|---|---|---|---|
| Kit – control | | | 0.52% | |
| Kit + control | | | 36% | |
| PBMC + FAS | | – | 13.7 | |
| | | + | 16.2 | |
| PBMC no IL-2 | | – | 9.5 | 1 |
| | | + | 16.2 | 1 |
| AZT | 1 | – | 15.1 | 1.6 |
| | | + | 13.7 | 0.8 |
| IG-07 | 100 | – | 54 | 5.7 |
| | | + | 64 | 3.9 |
| | 50 | – | 27 | 3.1 |
| | | + | 32.6 | 2 |
| IG-08 | 30 | – | 11.7 | 1.3 |
| | | + | 13.8 | 0.8 |
| | 15 | – | 18.4 | 1.9 |
| | | + | 29 | 1.8 |
| Cannabidiol | 30 | – | ND | |
| | | + | ND | |
| | 15 | – | ND | |
| | | + | ND | |

The flow cytometry data demonstrate that the IG compounds and cannabidiol are acting at the level of the cell cycle in PBMCs. This is consistent with the time-of-addition experiments demonstrating that the majority of the compounds could suppress virus replication if added very late in the virus replication cycle. The data is also consistent with the pretreatment time-of-addition assays, which suggest that although the antiviral activity could be modulated by pretreatment that there was a "global" mechanism of action responsible for the overall antiviral activity. The failure to correlate significant induction of apoptosis with the antiviral response further supports the hypothesis that it is an effect at the level of the cell cycle that is responsible for inhibition of virus replication rather than elimination of infected cell via apoptosis. Thus these studies would suggest that antiviral activity is directly correlated to cannabichromene cytostatic effects.

INCORPORATION BY REFERENCE

All sources (e.g., inventor's certificates, patent applications, patents, printed publications, repository accessions or records, utility models, world-wide web pages, and the like) referred to or cited anywhere in this document or in any drawing, Sequence Listing, or Statement filed concurrently herewith are hereby incorporated into and made part of this specification by such reference thereto.

GUIDE TO INTERPRETATION

The foregoing is an integrated description of the invention as a whole, not merely of any particular element of facet thereof. The description describes "preferred embodiments" of this invention, including the best mode known to the inventors for carrying it out. Of course, upon reading the foregoing description, variations of those preferred embodiments will become obvious to those of ordinary skill in the art. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law.

As used in the foregoing description and in the following claims, singular indicators (e.g., "a" or "one") include the plural, unless otherwise indicated. Recitation of a range of discontinuous values is intended to serve as a shorthand method of referring individually to each separate value falling within the range, and each separate value is incorporated into the specification as if it were individually listed. As regards the claims in particular, the term "consisting essentially of" indicates that unlisted ingredients or steps that do not materially affect the basic and novel properties of the invention can be employed in addition to the specifically recited ingredients or steps. In contrast, the terms "comprising" or "having" indicate that any ingredients or steps can be present in addition to those recited. The term "consisting of" indicates that only the recited ingredients or steps are present, but does not foreclose the possibility that equivalents of the ingredients or steps can substitute for those specifically recited.

What is claimed is:

1. A method for inhibiting the replication or proliferation of HIV within a host cell, the method comprising exposing at least one compound selected from cannabichromene derivatives to a host cell infected with HIV in amounts sufficient to inhibit the replication or proliferation of HIV within the host cell upon infection with HIV, wherein the cannabichromene derivative is selected from the group of cannabichromene derivatives consisting of those with the following formula:

wherein:
$R^1$ is:
a) H,
b) a $C_{1-4}$ alkyl group or ester thereof,
c) COOH,
d) OH,
e) a O—$C_{1-5}$ alkyl or alkanoyl, optionally substituted by mono- or di-methylamino or ethylamino groups,
f) a O—CO—$C_{3-10}$ alkyl group containing a carboxyl or amino group,
g)

wherein n=1 to 8
h) a p-aminobenzyl group or a $C_{1-7}$ aminoalkyl group or an organic or mineral acid addition salt thereof, an isocyanate or isothiocyanate derivative of the p-aminobenzyl or aminoalkyl group, a carboxyl terminated derivative of the aminoalkyl group having from 1 to 7 additional carbon atoms or a salt thereof, and an activated derivative of the carboxyl terminated derivative;
i) $R^1$ and $R^2$ may also be a substituent of the formula —O(CH$_2$)$_{3-5}$, wherein $R^1$ and $R^2$, together with the carbon atoms to which they are bonded, forms a ring where at least one hydrogen atom thereof is optionally substituted with a halogen;
j) a lactone; or
k) CH(CH$_3$)CO$_2$H or —OCOCH$_3$
$R^2$ is:
a) H, OH, COOH, or a halogen
b) $C_{1-6}$ carboxy or alkoxy group, or
c) $R^1$ and $R^2$ may also be a substituent of the formula —O(CH$_2$)$_{3-5}$, wherein $R^1$ and $R^2$, together with the carbon atoms to which they are bonded, forms a ring where at least one hydrogen atom thereof is optionally substituted with a halogen;
$R^3$ is:
a) (W)$_m$—Y—(Z)$_n$, wherein
W is a $C_{5-12}$ straight or branched alkyl, alkenyl, alkynyl, group, or mixture thereof, optionally substituted with at least one halogen,
Y is a bond, O, S, SO, SO$_2$, CO, NH, N($C_{1-6}$ alkyl), or NCS,
Z is:
i) a $C_{5-12}$ alkyl, alkenyl, alkynyl, group, or mixture thereof, optionally substituted with at least one halogen, optionally substituted with a terminal aromatic ring,
ii) CN$_{1-3}$, CO$_2$H, or CO$_2$C$_{1-4}$ alkyl, CONH$_2$, CONHC$_{1-4}$ alkyl, or CON(C$_{1-4}$ alkyl)$_2$, wherein each C$_{1-4}$ alkyl on the amide nitrogen can be the same or different, or
iii) a phenyl or benzyl group, optionally substituted with halo, $C_{1-6}$ alkyl, $C_{1-6}$ alkoxy, $C_{1-6}$ alkylthio, CN, CF$_3$, CO$_2$H, or CO$_2$C$_{1-4}$ alkyl, CONH$_2$, CONHC$_{1-4}$ alkyl, or CON(C$_{1-4}$ alkyl)$_2$, wherein each C$_{1-4}$ alkyl on the amide nitrogen can be the same or different, and
wherein
m and n are the same or different, and each is either 0 or 1,
b) a $C_{5-12}$ alkyl or haloalkyl group, optionally substituted with a terminal aromatic ring, CN$_{1-3}$, NCS, $CO_2H$, or $CO_2C_{1-4}$ alkyl, $CONH_2$, $CONHC_{1-4}$ alkyl, or $CON(C_{1-4}\text{ alkyl})_2$, wherein each $C_{1-4}$ alkyl on the amide nitrogen can be the same or different, or c) a $C_{5-12}$ alkene or alkyne group, optionally substituted with a halogen, dithiolene, terminal aromatic ring, $CN_{1-3}$, NCS, $CO_2H$, or $CO_2C_{1-4}$ alkyl, $CONH_2$, $CONHC_{1-4}$ alkyl, or $CON(C_{1-4}\text{ alkyl})_2$, wherein each $C_{1-4}$ alkyl on the amide nitrogen can be the same or different;

$R^6$ is selected from the group consisting of:
a) hydrogen,
b) hydroxy or lactone,
c) halo,
d) $C_{1-6}$ alkoxy, $C_{1-6}$ alkylthio, $C_{1-6}$ alkyl, or $C_{1-6}$ haloalkyl,
e) CN,
f) $N_3$,
g) $CO_2H$,
h) $CO_2$-$C_{1-4}$ alkyl,
i) C(Y)(Z)—OH,
j) C(Y)(Z)—O—$C_{1-4}$ alkyl, and
k) $C_{1-6}$ alkyl-$CO_2$—Y,
wherein Y and Z are each independently H or $C_{1-6}$ alkyl, $R^7$ is selected from the group consisting of:
a) hydrogen,
b) hydroxy or lactone,
c) halo,
d) $C_{1-6}$ alkoxy, $C_{1-6}$ alkylthio, $C_{1-6}$ alkyl, or $C_{1-6}$ haloalkyl,
e) CN,
f) $N_3$,
g) $CO_2H$,
h) $CO_2$-$C_{1-4}$ alkyl,
i) C(Y)(Z)—OH,
j) C(Y)(Z)—O—$C_{1-4}$ alkyl,
k) $C_{1-6}$ alkyl-$CO_2$—Y, and
l) =O or =S;
wherein Y and Z are each independently H or $C_{1-6}$ alkyl, $R^{12}$ and $R^{12'}$ together form =O or =S, or each is independently selected from the group consisting of:
a) hydrogen,
b) hydroxy or lactone,
c) halo,
b) $C_{1-6}$ alkoxy, $C_{1-6}$ alkylthio, $C_{1-6}$ alkyl, or $C_{1-6}$ haloalkyl,
c) CN,
d) $N_3$,
d) $CO_2H$,
e) $CO_2$-$C_{1-4}$ alkyl,
f) C(Y)(Z)—OH,
g) C(Y)(Z)—O—$C_{1-4}$ alkyl, and
h) $C_{1-6}$ alkyl-$CO_2$—Y,
wherein Y and Z axe each independently H or $C_{1-6}$ alkyl; and Q is O.

2. The method of claim 1, wherein $R^1$ is a lactone, H, OH, $OCH_3$, methyl, —CH($CH_3$)$CO_2H$, or —$OCOCH_3$.

3. The method of claim 1, wherein $R^2$ is a halogen, H, or COOH.

4. The method of claim 1, wherein $R^3$ is a $C_{5-12}$ alkyl, haloalkyl, alkenyl, haloalkenyl, alkynyl, or haloalkynyl group, or mixture thereof.

5. The method of claim 1, wherein $R^3$ is 1,1,5-trimethylhexyl, 1,1,5,5-tetramethylhexyl, or 1,1,5-trimethyl-hept-4-enyl.

6. The method of claim 1, wherein $R^6$ is H, OH, lactone, halogen, $C_{1-6}$ alkoxy, or $C_{1-6}$ alkyl.

7. The method of claim 1, wherein $R^7$ is H, OH, halogen, or COOH.

8. The method of claim 1, wherein $R^{12}$ is H, OH, lactone, halogen, $C_{1-6}$ alkoxy, or $C_{1-6}$ alkyl.

9. The method of claim 1, wherein $R^{12'}$ is H, OH, lactone, halogen, $C_{1-6}$ alkoxy, or $C_{1-6}$ alkyl.

10. The method of claim 1, wherein the bond between $C_7$ and $C_8$ is double bond.

11. The method of claim 1, wherein $R^6$ is $CH_3$, $R^7$ is H, $R^{12}$ and $R^{12'}$ are each $CH_3$, Q is oxygen, and the bond between $C_7$ and $C_8$ is a double bond.

12. The method of claim 1, wherein the O—$C_{1-5}$ alkyl compound of $R^1$ is $OCH_3$.

13. The method of claim 1, wherein the branched $C_{5-12}$ is 1S'$CH_3$, 2R'$CH_3$ dimethyl.

14. The method of claim 1, wherein the host cell is in vivo.

* * * * *